(12) United States Patent
Goble (10) Patent No.: US 7,214,224 B2
(45) Date of Patent: *May 8, 2007

(54) ELECTROSURGICAL SYSTEM

(75) Inventor: Colin Charles Owen Goble, Park Close Lodge (GB)

(73) Assignee: Gyrus Medical Limited, Cardiff (GB)

( * ) Notice: Subject to any disclaimer, the term of this patent is extended or adjusted under 35 U.S.C. 154(b) by 325 days.

This patent is subject to a terminal disclaimer.

(21) Appl. No.: 10/642,290

(22) Filed: Aug. 18, 2003

(65) Prior Publication Data

US 2004/0054365 A1 Mar. 18, 2004

(30) Foreign Application Priority Data

Sep. 18, 2002 (GB) .................................. 0221707.3

(51) Int. Cl.
*A61B 18/18* (2006.01)
(52) U.S. Cl. .............................. 606/34; 606/41; 606/37
(58) Field of Classification Search ............. 606/32–52
See application file for complete search history.

(56) References Cited

U.S. PATENT DOCUMENTS

| | | | |
|---|---|---|---|
| 4,427,006 A | | 1/1984 | Nottke |
| 5,269,780 A | * | 12/1993 | Roos ............................ 606/42 |
| 5,376,089 A | | 12/1994 | Smith |
| 5,383,874 A | | 1/1995 | Jackson et al. |
| 5,400,267 A | * | 3/1995 | Denen et al. .................. 702/59 |
| 5,460,629 A | * | 10/1995 | Shlain et al. .................. 606/46 |
| 5,540,683 A | * | 7/1996 | Ichikawa et al. .............. 606/40 |
| 5,573,424 A | | 11/1996 | Poppe |
| 5,591,551 A | | 1/1997 | Audett et al. |
| 5,743,903 A | * | 4/1998 | Stern et al. .................... 606/31 |
| 6,068,627 A | | 5/2000 | Orszulak et al. |
| 6,165,169 A | * | 12/2000 | Panescu et al. ................. 606/1 |
| 6,174,309 B1 | * | 1/2001 | Wrublewski et al. ......... 606/45 |
| 6,270,497 B1 | | 8/2001 | Sekino et al. |
| 6,306,131 B1 | * | 10/2001 | Hareyama et al. ............. 606/38 |
| 6,464,689 B1 | * | 10/2002 | Qin et al. ....................... 606/1 |
| 6,808,525 B2 | * | 10/2004 | Latterell et al. ............... 606/42 |
| 6,929,641 B2 | * | 8/2005 | Goble et al. .................. 606/37 |

FOREIGN PATENT DOCUMENTS

| | | |
|---|---|---|
| DE | 43 39 049 A1 | 5/1995 |
| DE | 4339049 A1 * | 5/1995 |
| WO | WO 97/14358 A1 | 4/1997 |
| WO | WO 97/24073 | 7/1997 |

* cited by examiner

*Primary Examiner*—Michael Peffley
(74) *Attorney, Agent, or Firm*—Nixon & Vanderhye P.C.

(57) ABSTRACT

An electrosurgical system includes a generator (10) for generating radio frequency power, an electrosurgical instrument (12) including at least two electrodes, and an identification element (80) representative of at least the number of electrodes present on the instrument. The generator (10) comprises an RF output stage having three or more output connections (62A, 62B, 62C), and a power supply (66) coupled to the output stage for supplying power to the output stage. The generator (10) also includes a controller (72) capable of varying the RF signal supplied to at least one of the three or more output connections (62A, 62B, 62C), and a switching circuit (62) for varying the connections between the power supply (66) and the three or more output connections. The generator (10) also includes a sensing circuit capable of sensing the identification element (80) carried by the instrument, and of sending a signal to the switching circuit (62) to set the switching circuit to a mode of operation depending on the number of electrodes present on the instrument (12).

22 Claims, 7 Drawing Sheets

ELECTROSURGICAL SYSTEM

BACKGROUND TO THE INVENTION

This invention relates to an electrosurgical system comprising an electrosurgical generator and a handpiece including electrosurgical electrodes. Such systems are commonly used for the cutting and/or coagulation of tissue in surgical intervention, most commonly in "keyhole" or minimally-invasive surgery, but also in laparoscopic or "open" surgery.

It is known to provide electrosurgical generators with different radio frequency signals for cutting and coagulation, and also to switch between two different instruments, e.g. bipolar and monopolar instruments. In a first type of prior art system, it is also known to provide an electrosurgical instrument with a single electrode, and switching means on the instrument to connect the electrode alternately to either a cutting output or to a coagulating output from the generator. Examples of these types of instrument are to be seen in U.S. Pat. No. 4,427,006, U.S. Pat. No. 5,376,089 and U.S. Pat. No. 5,573,424.

Alternatively, in a second type of prior art system, it is known to provide an instrument with multiple electrodes, and to provide switching means on the instrument to be able to connect the signal from the generator to different electrodes or combinations of electrodes. Examples of this type of instrument are to be seen in U.S. Pat. No. 5,269,780 and U.S. Pat. No. 5,951,551. The disadvantage of all of these prior art systems is that it is not possible to optimise both the signal supplied by the generator and the choice of electrodes. In the case of the first type of prior art system, the use of a single electrode means that its design must always be a compromise between designs suited to cutting and coagulation. In the case of the second type of prior art, the instrument uses the same output signal from the generator for whichever combination of electrodes is deployed. U.S. Pat. No. 6,270,497 discloses a device which switches between coagulation and cutting operations, but which is relatively complicated in design.

It is an aim of the present invention to provide an electrosurgical system which attempts to provide an optimised combination of electrode combination in the handpiece and electrosurgical signal from the generator, and which is relatively simple in operation.

SUMMARY OF THE INVENTION

Accordingly there is provided an electrosurgical system including a generator for generating RF power, and an electrosurgical instrument including at least two electrodes, and an identification element carried by the instrument and being representative of at least the number of electrodes present on the instrument,
the generator comprising:
(i) an RF output stage having at least a pair of RF output lines,
(ii) a power supply coupled to the output stage for supplying power to the output stage,
(iii) a controller capable of varying an RF signal supplied to the RF output lines,
(iv) a switching circuit having at least three output connections, each of at least two of which being in electrical connection with a respective one of the at least two electrodes, and
(v) a sensing circuit adapted to sense the identification element carried by the instrument,
the arrangement being such that the switching circuit operates to connect the RF output lines to two or more of the at least three output connections depending on the identification element carried by the instrument.

In one convenient arrangement, the identification element is a resistor, and the sensing circuit is adapted to sense the resistance of the identification element. Alternatively, the identification element is a capacitor, and the sensing circuit is adapted to sense the capacitance of the identification element. In a preferred arrangement, the sensing circuit includes an inductor such as to form a resonant circuit with the identification element, the sensing circuit being adapted to determine the resonant frequency of the resonant circuit so as to identify the identification element.

In this way, the electrosurgical signal employed can be optimised depending on the instrument connected thereto, and similarly the electrodes can be designed specifically for the function they are chosen to perform.

Preferably, the controller automatically adjusts the RF power supplied to at least one of the three or more output connections to limit the peak generator output voltage to at least a first value when a first combination of electrodes is selected by the switching circuit, and to at least a second value when a second combination of electrodes is selected by the switching circuit.

In one arrangement, two of the three or more electrodes are in the form of jaws adapted to grasp tissue therebetween, and the third electrode is mounted on one of the jaws, separated therefrom by an insulating member. The third electrode may be mounted on the internal or external face of said one jaw, or even at the tip thereof. The third electrode may be mounted on said one jaw in a recess therein, such that only a part of the electrode protrudes from the jaw. This type of arrangement applies to forceps or scissors-type instruments, suitable for grasping and/or cutting tissue.

Alternatively, at least one, and preferably at least three, of the electrodes is in the form of a hook. Hook and needle-type instruments are also common in laparoscopic surgery, and may be employed in the present invention. Conveniently one of the hook electrodes extends distally beyond the other electrodes. Preferably, the electrode which extends distally beyond the other electrodes is positioned centrally between the other electrodes.

In one construction, at least one of the electrodes is longitudinally movable such that it can be extended and retracted with respect to the other electrodes. In this way, tissue can be held in the gap formed between the retractable electrode and the other electrodes. As before, the longitudinally-movable electrode is preferably positioned centrally between the other electrodes.

According to a further aspect of the invention, there is provided an electrosurgical system including a generator for generating RF power, and a plurality of electrosurgical instruments, the plurality of electrosurgical instruments including at least one electrosurgical instrument having two electrodes, and at least one electrosurgical instrument having at least three electrodes, each of the plurality of electrosurgical instruments having an identification element carried by the instrument and being representative of at least the number of electrodes present on the instrument,
the generator comprising:
(i) an RF output stage having at least a pair of RF output lines,
(ii) a power supply coupled to the output stage for supplying power to the output stage,
(iii) a controller capable of varying an RF signal supplied to the RF output lines, (iv) a switching circuit having at least three output connections, and
(v) a sensing circuit adapted to sense the identification element carried by the instrument, the arrangement being such that, when the sensing circuit senses an identification element indicating an electrosurgical instrument having two electrodes, the switching circuit is set to a first mode of operation, and, when the sensing circuit senses an identification element indicating an electrosurgical instrument having at least three electrodes, the switching circuit is set to a second mode of operation.

BRIEF DESCRIPTION OF THE DRAWINGS

The invention will now be further described, by way of example only, with reference to the accompanying drawings, in which.

DESCRIPTION OF PREFERRED EMBODIMENTS

Figure 1:
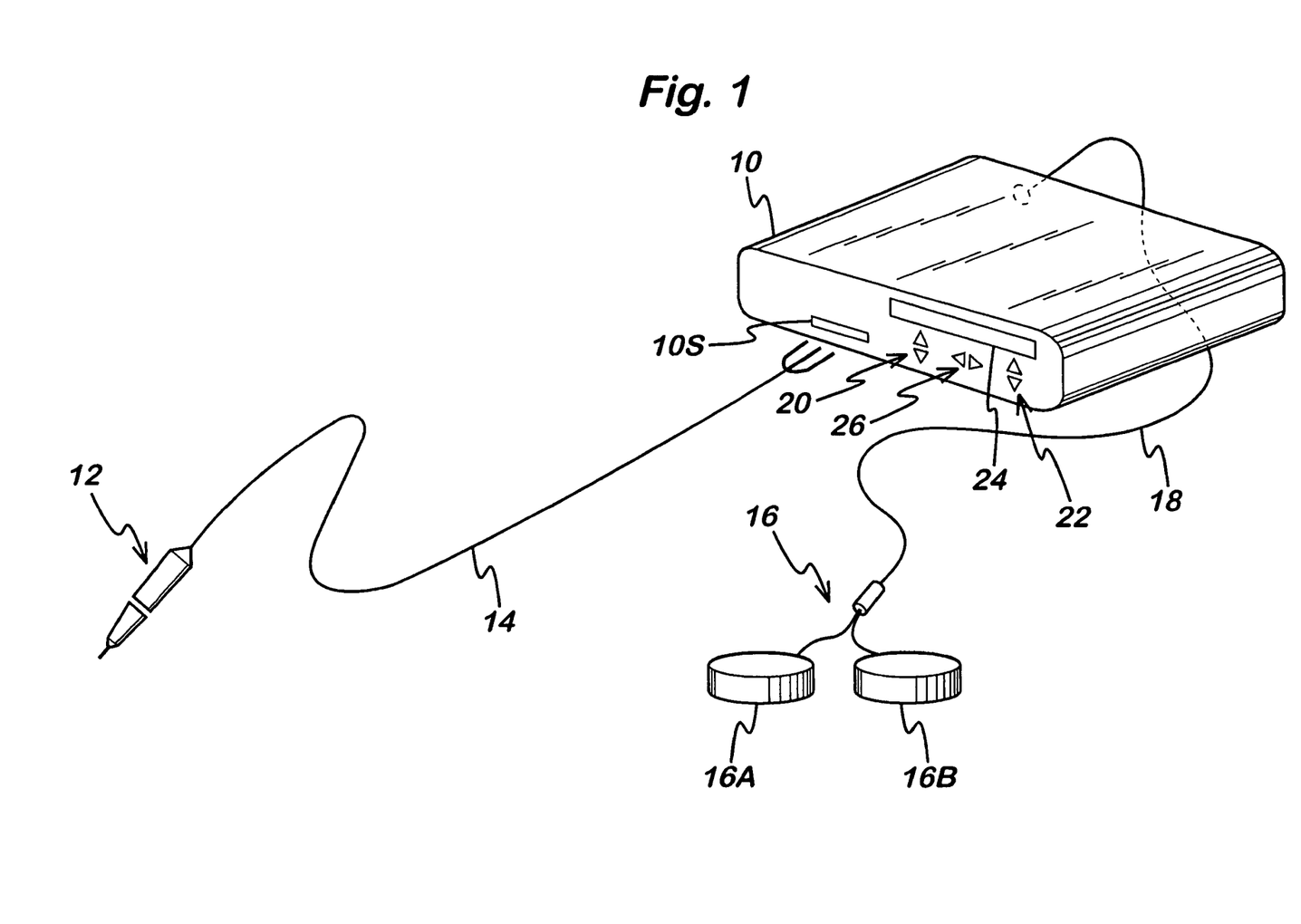
FIG. 1 is a schematic diagram of an electrosurgical system constructed in accordance with the present invention.

Referring to FIG. 1, a generator 10 has an output socket 10S providing an RF output for an instrument 12 via a connection cord 14. Activation of the generator 10 may be performed from the instrument 12 via a connection in cord 14 or by means of a footswitches unit 16, as shown, connected to the rear of the generator by a footswitch connection cord 18. In the illustrated embodiment, the footswitch unit 16 has two footswitches 16A and 16B for selecting a coagulation mode and a cutting mode of the generator 10 respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
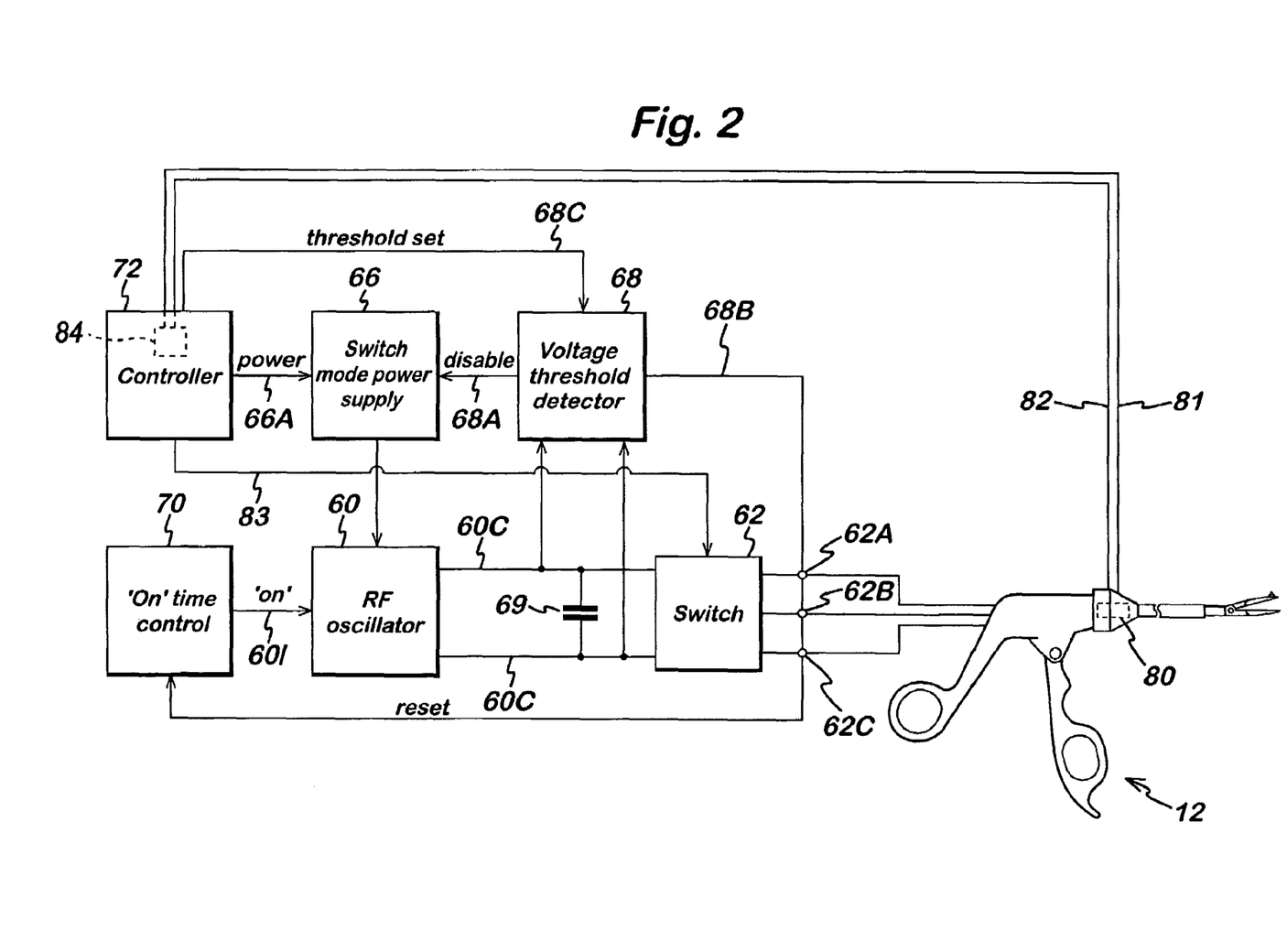
FIG. 2 is a block diagram of the generator of FIG. 1, shown with an electrosurgical instrument connected thereto.
Figure 11:
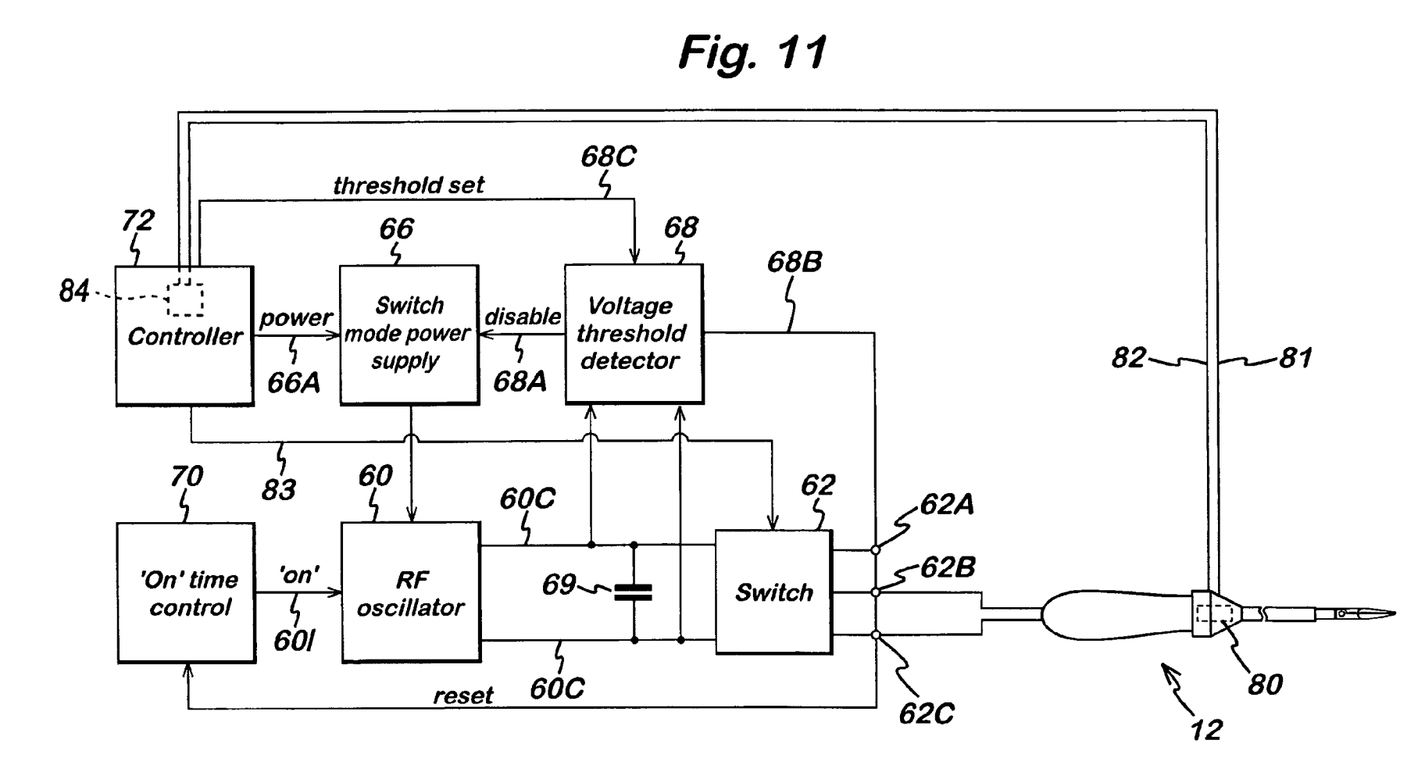
FIGS. 11 and 12 are block diagrams of the generator of FIG. 1, shown with different types of electrosurgical instrument connected thereto.
Figure 12:
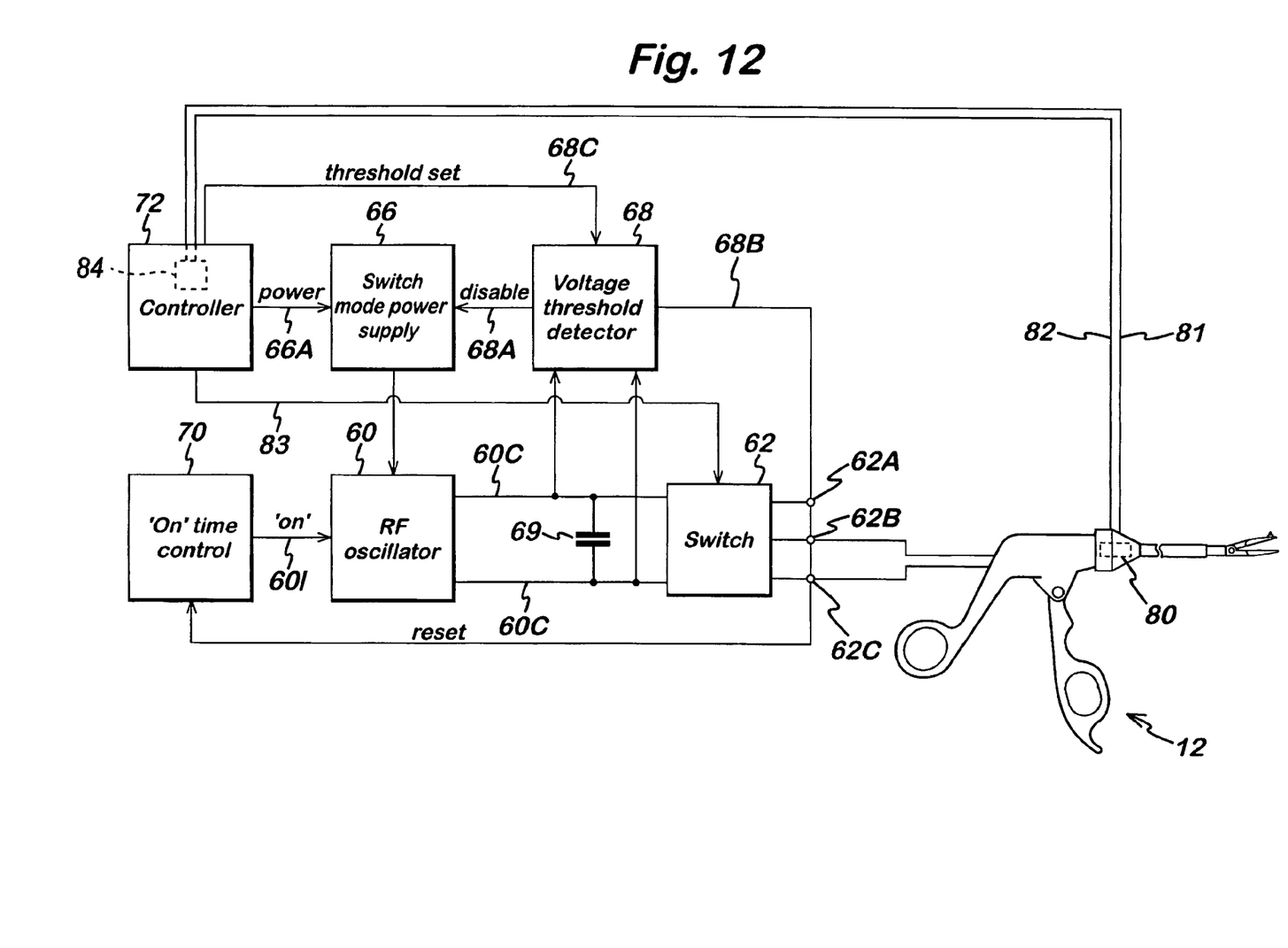

Referring to FIG. 2, the generator comprises a radio frequency (RF) power oscillator 60 having a pair of output lines 60C for coupling via switching circuit 62 to the instrument 12. At least output lines 60C comprise an RF output stage. Switching circuit 62 has three output connections 62A, 62B and 62C for connection to the electrodes of the instrument as will be described later. A capacitor 69 is connected between output lines 60C, as shown in FIGS. 2, 11 and 12. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range from 25 to 50 kHz. Coupled across the output lines 60C is a voltage threshold detector 68 having a first output 68A coupled to the switched mode power supply 16 and a second output 68B coupled to an "on" time control circuit 70. A micro-processor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RE output voltage limits.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). A constant output voltage threshold is set independently of the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range from 250 or 300 volts to 600 volts. These voltage values are peak values. Their being peak values means that for desiccation at least it is preferable to have an output RF wave-from form of low crest factor to give maximum power before the voltage is clamped at the values given. Typically a crest factor of 1.5 or less is achieved.

When the generator 10 is first activated, the status of the control input 60I of the RF oscillator 60 (which is connected to the "on" time control circuit 70) is "on", such that the power switching device which forms the oscillating element of the oscillator 60 is switched on for a maximum conduction period during each oscillation cycle. The power delivered to the load depends partly on the supply voltage applied to the RF oscillator 60 from the switched mode power supply 66, and partly on the load impedance 64. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply 66 is disabled, so that the voltage supplied to oscillator 60 begins to fall. The operation of the generator in this way is described in detail in our European Patent application no. 0754437, the disclosure of which is hereby incorporated by way of reference.

Instrument 12 carries an identification element 80, such as a resistor, capacitor or EPROM. Identification systems for medical instruments are known in the art, and one type of identification system is described in our earlier patent U.S. Pat. No. 6,074,386. The identification element 80 is interrogated by the controller 72, via lines 81 and 82. The controller 72 can include a sensing circuit 84 adapted to sense the identification element 80 carried by the instrument 12. If the identification element 80 is a resistor, the sensing circuit 84 is adapted to sense the resistance of the identification element 80. Similarly, if the identification element 80 is a capacitor, the sensing circuit 84 is adapted to sense the capacitance of the identification element 80. Finally, if the sensing circuit includes an inductor so as to form a resonant circuit with the identification element 80, the sensing circuit is adapted to determine the resonant frequency of the resonant circuit so as to identify the identification element 80. The identification element provides information as to the type of instrument connected to the generator, and in particular to the number of electrodes present on the instrument. The controller 72, having interrogated the identification element 80 and determined the number of electrodes present on the instrument 12, sends a signal via line 83 to the switch 62, in order to control the operation thereof. The settings of the switch 62 for various types of instrument will be explained in more detail later.

Figures 3, 3A:
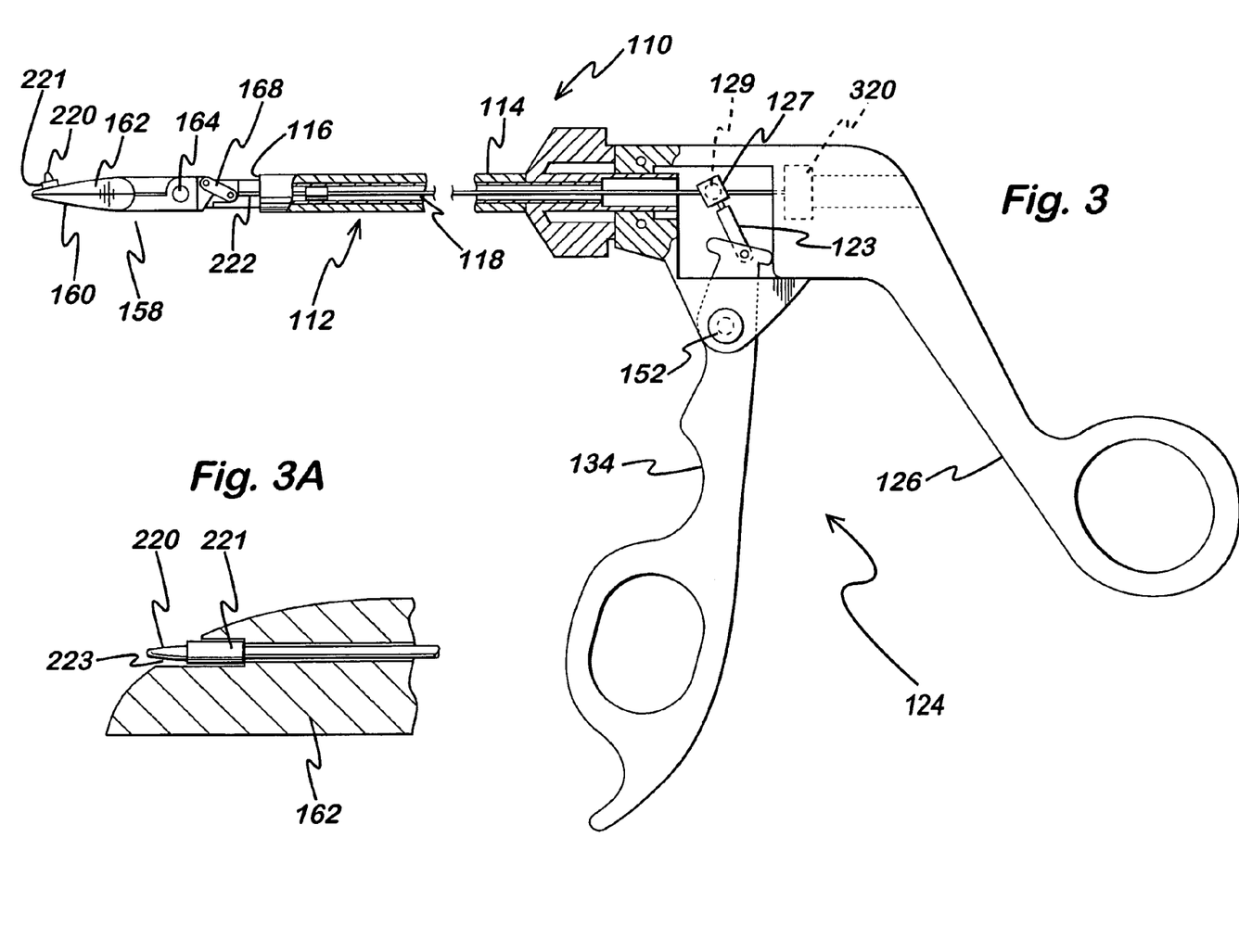
FIG. 3 is a schematic side view, shown partly in section, of a forceps-type instrument for use in the system of FIG. 1.
FIG. 3a is a sectional side view showing an alternative embodiment of jaw for the instrument of FIG. 3.

FIG. 3 shows one type of instrument 12 which can be connected to the generator 10. The device is a bipolar forceps shown generally at 110. The forceps has an elongated tubular member 112 with a proximal end 114, a distal end 116, and a lumen 118 which extends for the entire length of the tubular member. At the proximal end 114 of the tubular member 112 is a scissors-type handle assembly 124 with a first handle 126 and a second handle 134. The second handle 134 is pivotable with respect to the first, about a pivot pin 152. In a known design of actuation mechanism, the second handle 134 has a pin 123 affixed to the top thereof, such that movement of that handle causes a corresponding movement to a sphere 129 supported in a U-shaped cradle 127.

Figure 4:
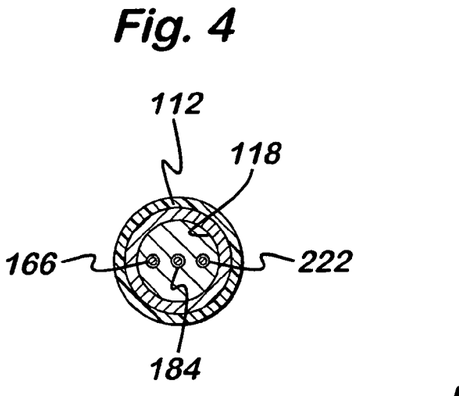
FIG. 4 is a sectional view longitudinally through the instrument of FIG. 3, FIGS. 5A and 5B are schematic views of the switching circuitry of FIG. 2, shown in first and second alternative conditions.

Fitted into the distal end 116 of the tubular member 112 is a forceps jaw assembly 158 comprising a first jaw member 160 and a second jaw member 162, pivotally joined to each other by an insulated rivet 164. The jaw member 162 is provided with a cutting electrode 220, isolated from the jaw member 162 by a ceramic insulator 221. As shown in FIG. 4, three rigid electrically conductive rods 166, 184 and 222, each covered with a layer of electrical insulation, extend through the lumen 118 of the tubular member 112. The rods 166, 184 are pivotally connected to the respective jaw members 160, 162 by rigid links 168, whilst the rod 222 is connected by means of a wire (not shown) to the electrode 220. The proximal ends of the rods 166, 184 and 222 extend from the tubular member 112 through the sphere 129 and terminate in a connector 320. The output connections 62A, 62B and 62C from the generator 10 are thereby electrically connected to the rods 166, 184 and 222 respectively, via the lead 14 and the connector 320.

Figure 5A:
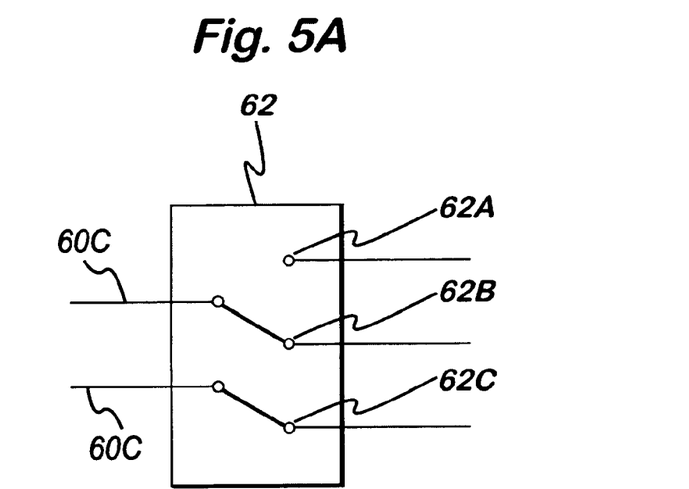

The operation of the instrument will now be described. The identification element 80 identifies the instrument 12 to the controller 72 as an instrument having three electrodes, and the controller sets the operating parameters of the switch 62 accordingly. When it is desired to operate the instrument 12 in a cutting mode, footswitch 16A is depressed which causes a signal to be sent to the controller 72 which sets the switching circuit 62 its "cut" position. This is illustrated in FIG. 5A, in which the signals from the oscillator 60 are connected between output connections 62B and 62C. This means that the RF signal is applied between the cutting electrode 220 (via rod 222) and the jaw member 162 (via rod 184). At the same time as the controller 72 sets the switching circuit to the position in FIG. 5A, it also sends a signal via line 68C to the voltage threshold detector 68 to set the peak output voltage limit to a relatively high "cutting" level. The control of this cutting signal is described in more detail in EP 0754437, referred to earlier.

Figure 5B:
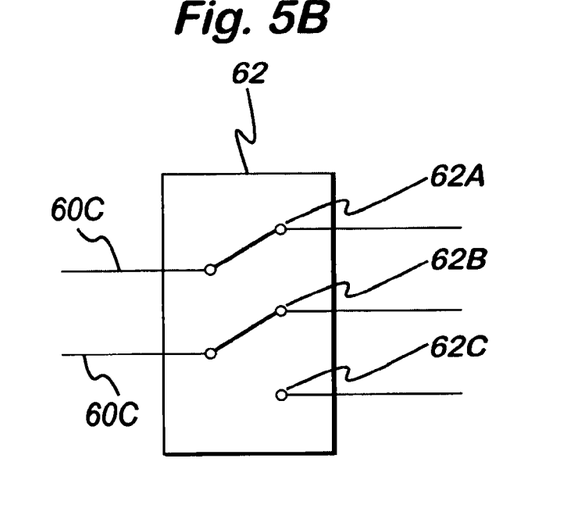

Alternatively, when it is desired to operate the instrument 12 in a coagulation mode, the footswitch 16B is depressed which causes the controller 72 to set the switching circuit 62 to its "coag" position, as illustrated in FIG. 5B. In this set-up, the signals from the oscillator 60 are connected between the output connections 62A and 62B. This means that the RF signal is applied between the two jaw members 160 and 162 (via the rods 166 and 184). At the same time, the controller 72 sends a signal to the voltage threshold detector 68 to set the peak output voltage limit to a relatively lower "coagulating" level, again as more particularly described in EP 0754437. The jaw members 160 and 163 can be opened and closed by manipulating the handle 134 causing translational movement of the sphere 129 and the rods 166 and 184.

It is envisioned that, as an alternative to leaving output connection (and hence the jaw member 160) to float electrically when the switching circuit is in its "cut" position as illustrated in FIG. 5A, the output connections 62A and 62B (and hence both the jaw members 160 and 162) could be commonly connected. In this instance the capacitor 69, connected across the output lines 60C of the oscillator 60, may be dispensed with.

It will be seen that, not only is the RF signal different for cutting and coagulation, but also the electrodes used to perform each operation are different. Cutting is performed using the relatively small cutting electrode 220, using the relatively large surface area of the jaw member 162 as the return electrode. Conversely, coagulation is performed, not using the cutting electrode 220, but using the first and second jaw members 160 and 162. In this way, both the electrical signal and the choice of electrode can be optimised, depending on the function to be performed.

In alternative embodiments of the device of FIGS. 3 and 4, the cutting electrode 220 may be located at the tip of the jaw member 162, or even on the inside jaw face as opposed to the outside jaw face illustrated in FIG. 3. Alternatively, the cutting electrode 220 and the ceramic insulator 221 may be mounted on the jaw member 162 in a recess 223 provided thereon. This is the arrangement illustrated in FIG. 3a. The operation of the instrument will be the same, and the location of the cutting electrode may merely depend on the type of procedure undertaken.

Figure 6:
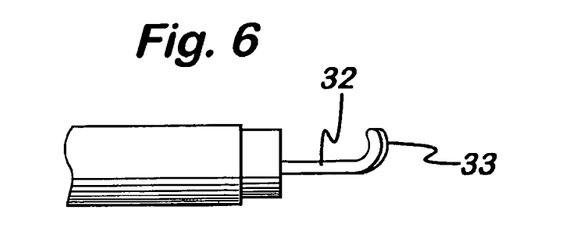
FIGS. 6 and 7 are side and plan views, respectively, of a part of an alternative instrument for use in the system of FIG. 1.
Figure 7:
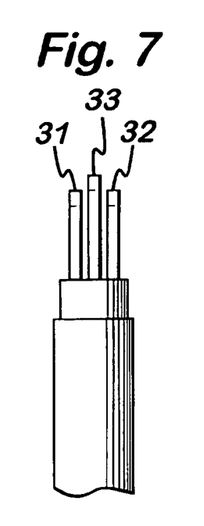

FIGS. 6 and 7 show an alternative embodiment, in which the jaw members of the device of FIG. 3 are replaced by hook electrodes. These types of instrument are particularly suited to procedures such as prostatectomy and nephrectomy. First and second outside hook electrodes 31 and 32 are connected to the output connections 62A and 62B respectively, whilst a central cutting hook electrode 33 is connected to the output connection 62C. The cutting hook electrode 33 protrudes slightly further forward than the outside electrodes 31 and 32, as shown in FIG. 6. As before, the interrogation of the identification element 80 will indicate to the controller 72 that the instrument 12 has three electrodes. When the instrument is to be used for cutting, the switching circuit 62 is set to the position shown in FIG. 5A, and the cutting hook electrode 33 is energised with a cutting RF signal, with one or both of the outside hook electrodes acting as the return electrode. When coagulation is desired, the switching circuit is set to the position shown in FIG. 5B, such that a coagulating RF signal is supplied to both of the outside hook electrodes 31 and 32.

Figure 7A:
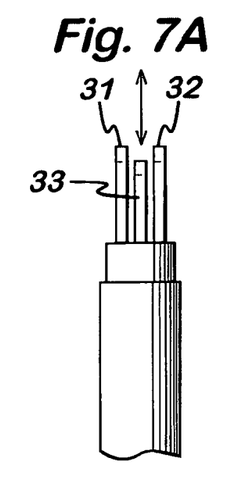
FIG. 7a is a plan view of an alternative embodiment of the instrument of FIGS. 6 and 7.

In further alternative embodiments of the invention, either the central cutting electrode 33 or the outside electrodes 31 and 32 can be made extendible and retractable, or the outside electrodes can be made jaw-like in order to spread or grasp tissue to be cut or coagulated. FIG. 7a shows a variation on the device of FIGS. 6 and 7 in which the central hook electrode 33 is movable longitudinally with respect to the outside electrodes 31 and 32. In FIG. 7a the central electrode 33 is shown retracted behind the outside electrodes 31 and 32, such as would be the case when coagulating using the outside electrodes or cutting by pulling the tissue towards the central cutting electrode 33.

Figure 8:
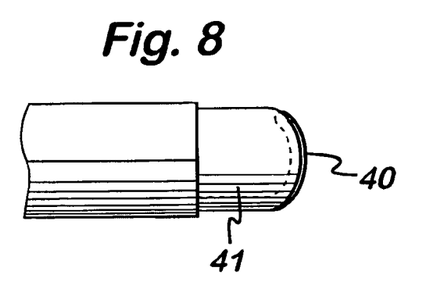
FIG. 8 is a side view of a part of a further alternative instrument for use in the system of FIG. 1, the instrument being shown in a retracted position.
Figure 9:
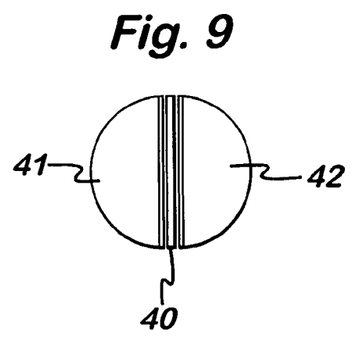
FIG. 9 is an end view of the instrument of FIG. 8.
Figure 10:
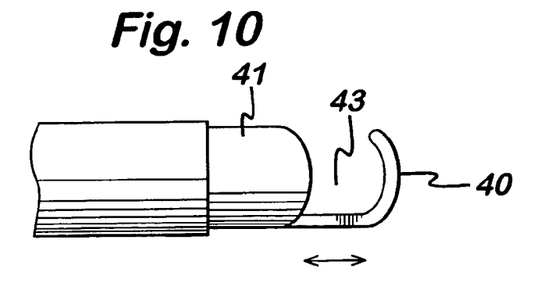
FIG. 10 is a side view of the instrument of FIG. 8, shown in an extended position.

In a further embodiment, illustrated in FIGS. 8 to 10, a central extendible hook electrode 40 is provided between stationary outside electrodes 41 and 42. In its retracted position, shown in FIG. 8, the central electrode 40 protrudes only slightly beyond the outside electrodes 41 and 42. In this position, the instrument may be used as a tissue cutter, with the central electrode 40 being supplied with a cutting RF signal from the generator 10, and one or both of the outside electrodes 41 and 42 acting as return electrodes. The central electrode 40 may also be extended, as shown in FIG. 10, and then retracted to hold tissue in the gap 43 created between the central hook electrode and the outside electrodes 41 and 42. By supplying a coagulating RF signal to the outside electrodes 41 and 42 (the switching circuit connecting the oscillator 60 to the output connections 62A and 62B as previously described), the tissue held in the gap 43 can be coagulated or desiccated. Alternatively, a cutting RF signal is supplied to the central hook electrode 40 (the switching circuit connecting the oscillator 60 to the output connections 62A and 62C), and the electrode 40 is retracted in order to cut through the tissue in the gap 43.

FIGS. 11 and 12 show alternative instruments connected to the generator 10, these instruments having only two electrodes. The controller 72 interrogates the identification element 80 within the instrument 12, which identifies the instrument as only having two electrodes, as well as the type of instrument present. In FIG. 11 the instrument is identified as being a two-electrode instrument capable of both cutting and coagulation, and so the controller 72 sends a signal via the line 83 to the switch 62 so that it is set into the position depicted in FIG. 5A for both cutting and coagulation operations. Whether the RF signal supplied from the oscillator 60 is a relatively high voltage "cutting" signal, or a relatively low voltage "coagulation" signal, the signal is supplied across the output connections 62B and 62C, and the switch 62 is inhibited from switching to the setting illustrated in FIG. 5B. This is different from the situation with reference to the three-electrode instruments described previously, and means that the generator 10 is capable of being used interchangeably with either two-electrode or three-electrode instruments, without any need for the manual adjustment of the settings thereof.

FIG. 12 shows a coagulation only instrument connected to the generator 10. This instrument also has two electrodes, and the interrogation of the identification element 80 will result in a similar setting to that described above with reference to FIG. 11. However, as the identification element 80 will identify the instrument 12 as a coagulation only instrument, the controller 72 will also be set to a condition in which the supply of high frequency "cutting" voltages will be inhibited.

As can be seen from the above, the combination of the identification element 80 with the switch 62 allows a variety of different instruments to be used with the generator 10, without the requirement for any manual setting or adjustment of the generator whatsoever. Those instruments capable of taking advantage of the switching of the output connections of the generator 10 will do so, while more simple devices will also function satisfactorily without the worry that they will receive inappropriate signals from the generator.

The invention claimed is:

1. An electrosurgical system including a generator for generating radio frequency (RF) power, and an electrosurgical instrument including at least two electrodes, and an identification element carried by the instrument and being representative of at least the number of electrodes present on the instrument, the generator comprising:
(i) an RF output stage having at least a pair of RF output lines,
(ii) a power supply coupled to the output stage for supplying power to the output stage,
(iii) a controller capable of varying an RF signal supplied to the RF output lines, so as to be capable of supplying either a cutting RF waveform or a coagulating RF waveform, and
(iv) a switching circuit having at least three output connections, at least two being in electrical connection with respective ones of the at least two electrodes, and
(v) a sensing circuit adapted to sense the identification element carried by the instrument, the switching circuit being operated to connect the RF output lines to two or more of the at least three output connections, depending on the particular identification element carried by the instrument, wherein the controller is arranged such that, when the identification element indicates that the electrosurgical instrument includes at least three electrodes, the switching circuit is operated to supply the cutting RF waveform between a first pair of the electrosurgical instrument's electrodes and the coagulating RF waveform between a second pair of the electrosurgical instrument's electrodes, but where the identification element indicates that the electrosurgical instrument includes only two electrodes, the switching circuit is operated to supply both the cutting RF waveform and the coagulating RF waveform to the same pair of electrodes.

2. A system according to claim 1 wherein the identification element is a resistor and the sensing circuit is adapted to sense the resistance of the identification element.

3. A system according to claim 1 wherein the identification element is a capacitor and the sensing circuit is adapted to sense the capacitance of the identification element.

4. A system according to claim 3 wherein the sensing circuit includes an inductor such as to form a resonant circuit with the identification element, the sensing circuit being adapted to determine the resonant frequency of the resonant circuit so as to identify the identification element.

5. A system according to claim 1, wherein the controller automatically adjusts the radio frequency power supplied to at least one of the three or more output connections to limit the peak generator output voltage to at least a first value when a first combination of electrodes is selected by the switching circuit, and to at least a second value when a second combination of electrodes is selected by the switching circuit.

6. A system according to claim 1, wherein two of the three or more electrodes are in the form of jaws adapted to grasp tissue therebetween.

7. A system according to claim 6, wherein the third electrode is mounted on one of the jaws, separated therefrom by an insulating member.

8. A system according to claim 7, wherein the third electrode is mounted on an external face of one of the jaws.

9. A system according to claim 7, wherein the third electrode is mounted on an internal face of one of the jaws.

10. A system according to claim 7, wherein the third electrode is mounted at the tip of one of the jaws.

11. A system according to claim 1, wherein at least one of the electrodes is in the form of a hook.

12. A system according to claim 11, wherein at least three of the electrodes are in the form of a hook.

13. A system according to claim 1, wherein at least two of the switching circuit's output connections are electrically connected to one another.

14. A system according to claim 1, wherein the first pair of electrodes includes an electrode that is also included in the second pair of electrodes.

15. An electrosurgical system including a generator for generating radio frequency (RF) power, and an electrosurgical instrument including at least two electrodes, and an identification element carried by the instrument and being representative of at least the number of electrodes present on the instrument, the generator comprising:
   (i) an RF output stage having at least a pair of RF output lines,
   (ii) a power supply coupled to the output stage for supplying power to the output stage,
   (iii) a controller capable of varying an RF signal supplied to the RF output lines, so as to be capable of supplying either a cutting RF waveform or a coagulating RF waveform, and
   (iv) a switching circuit having at least three output connections, at least two being in electrical connection with a respective one of the at least two electrodes, and
   (v) a sensing circuit adapted to sense the identification element carried by the instrument,
   the switching circuit being operated to connect the RF output lines to two or more of the at least three output connections, depending on the particular identification element carried by the instrument, so as to supply the cutting RF waveform between a first pair of the instrument's electrodes and the coagulating RF waveform between a second pair of the instrument's electrodes when the identification element indicates that the electrosurgical instrument includes at least three electrodes, and to supply both the cutting RF waveform and the coagulating RF waveform to the same pair of the instrument's electrodes where the identification element indicates that the electrosurgical instrument includes only two electrodes, and
   wherein at least one of the electrodes being in the form of a hook, at least one hook electrode extending distally beyond the other electrodes.

16. A system according to claim 15, wherein there is a centrally positioned electrode extending distally beyond the other electrodes.

17. An electrosurgical system including a generator for generating radio frequency (RF) power, and an electrosurgical instrument including at least two electrodes, and an identification element carried by the instrument and being representative of at least the number of electrodes present on the instrument, the generator comprising:
   (i) an RF output stage having at least a pair of RF output lines,
   (ii) a power supply coupled to the output stage for supplying power to the output stage,
   (iii) a controller capable of varying an RF signal supplied to the RF output lines, so as to be capable of supplying either a cutting RF waveform or a coagulating RF waveform, and
   (iv) a switching circuit having at least three output connections, at least two being in electrical connection with a respective one of the at least two electrodes, and
   (v) a sensing circuit adapted to sense the identification element carried by the instrument,
   the switching circuit being operated to connect the RF output lines to two or more of the at least three output connections depending on the particular identification element carried by the instrument, so as to supply the cutting RF waveform between a first pair of the instrument's electrodes and the coagulating RF waveform between a second pair of the instrument's electrodes when the identification element indicates that the electrosurgical instrument includes at least three electrodes, and to supply both the cutting RF waveform and the coagulating RF waveform to the same pair of the instrument's electrodes where the identification element indicates that the electrosurgical instrument includes only two electrodes, and
   wherein at least one of the electrodes is longitudinally movable such that it can be extended and retracted with respect to the other electrodes.

18. A system according to claim 17, wherein the longitudinally movable electrode is positioned centrally between the other electrodes.

19. An electrosurgical system including a generator for generating radio frequency (RF) power, and a plurality of electrosurgical instruments, the plurality of electrosurgical instruments including at least one electrosurgical instrument having two electrodes, and at least one electrosurgical instrument having at least three electrodes, each of the plurality of electrosurgical instruments having an identification element carried by the instrument and being representative of at least the number of electrodes present on the instrument, the generator comprising:
   (i) an RF output stage having at least a pair of RF output lines,
   (ii) a power supply coupled to the output stage for supplying power to the output stage,
   (iii) a controller capable of varying an RF signal supplied to the RF output lines, and
   (iv) a switching circuit having at least three output connections, so as to be capable of supplying either a cutting RF waveform or a coagulating RF waveform, and
   (v) a sensing circuit adapted to sense the identification element carried by the instruments,
   the switching circuit being operated, such that when the sensing circuit senses an identification element indicating an electrosurgical instrument having two electrodes, the switching circuit is set to a first mode of operation to supply both the cutting RF waveform and the coagulating RF waveform to the same pair of the instrument's electrodes, and when the sensing circuit senses an identification element indicating an electrosurgical instrument having at least three electrodes, the switching circuit is set to a second mode of operation to supply the cutting RF waveform between a first pair of the instrument's electrodes and the coagulating RF waveform between a second pair of the instrument's electrodes.

20. A system according to claim 19, wherein the first pair of electrodes includes an electrode that is also included in the second pair of electrodes.

21. An electrosurgical system comprising:
an electrosurgical instrument including at least two electrodes and using radio frequency (RF) power to operate,
an identification element carried by the electrosurgical instrument that is representative of at least the number of electrodes present on the instrument,
a power supply for supplying an RF signal that is either a cutting RF waveform or a coagulating RF waveform,
an RF output stage coupled to the power supply and having at least a pair of RF output lines,
a controller capable of varying the RF signal supplied to the RF output lines, so as to be capable of supplying either the cutting RF waveform or the coagulating RF waveform,
a switching circuit having at least three output connections, at least two being in electrical connection with respective ones of the at least two electrodes, and
a sensing circuit adapted to sense the identification element carried by the instrument,
the switching circuit being operated to connect the RF output lines to two or more of the at least three output connections, depending on the particular identification element carried by the instrument,
wherein the controller is arranged such that, when the identification element senses that the electrosurgical instrument includes at least three electrodes, the switching circuit is operated to supply the cutting RF waveform between a first pair of the instrument's electrodes, and the coagulating RF waveform is supplied between a second pair of the instrument's electrodes, but when the identification element senses that the electrosurgical instrument includes only two electrodes, the switching circuit is operated to supply both the cutting RF waveform and the coagulating RF waveform to the same pair of the instrument's electrodes.

22. A system according to claim 21, wherein the first pair of electrodes includes an electrode that is also included in the second pair of electrodes.

* * * * *